Feb. 23, 1943. G. R. FOWLER Plant Pat. 567
PEACH TREE
Filed Nov. 4, 1941
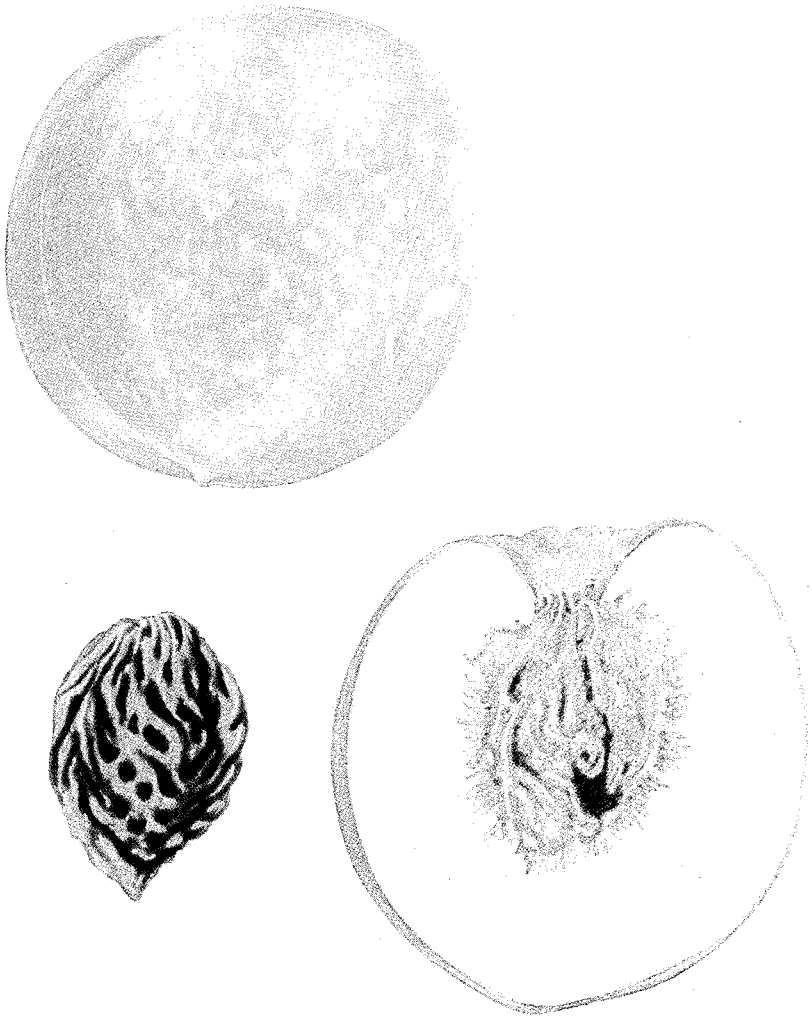
INVENTOR
George R Fowler
By Orville M Kile
PLANT PATENT AGENT Patented Feb. 23, 1943

Plant Pat. 567

UNITED STATES PATENT OFFICE

567

PEACH TREE

George R. Fowler, Marlboro, N. Y.

Application November 4, 1941, Serial No. 417,841

1 Claim. (Cl. 47—62)

My new invention relates to improvements in peach trees, with particular reference to the fruit thereof.

This new variety of peach tree developed in my orchards at Marlboro, N. Y. When a South Haven tree froze back, a new shoot appeared below the bud, and this bud developed into my new variety. My new variety therefore is either a seedling or a sport of a seedling, and in either case the parentage is unknown.

After observing the variety for a few years and recognizing that it had superior qualities, I budded a number of young trees in my orchard. The fruit from these trees has sold at a price much above the average market price for other peaches of similar type, further testifying to its superior quality.

The fruit is highly colored, very large, and of uniform size and shape, enabling it to make a good appearance. It has an excellent flavor which differs somewhat from other peaches. Its firm texture and relatively tough skin make it an excellent shipper.

It comes a little later than the J. H. Hale and the Elberta, usually about a week later.

The original illustrations making a part of this application show a side view and a cross section view of the fruit and a view of the seed of this variety, in approximately natural colors and size.

Following is a detailed description of the tree and fruit of this new variety. Color plate references indicate Ridgway's Color Standards and Nomenclature. Where no plate references are given, the ordinary dictionary meaning of the colors is intended.

*The tree*

Growth: Very vigorous; open and spreading, with round top.

Hardiness: Very hardy.

Bearing habits: Regular and heavy bearer of consistently large fruits.

Disease resistance: Healthy in every way; resistant to usual diseases of peach trees.

Wood: Trunk smooth; medium in size; strong; dark in color and usually with reddish tinge on side next to sun.

Leaves:

*Size.*—Large, measuring 6½ inches to 7 inches long and 1¾ inches to 2⅛ inches wide.

*Shape.*—Elliptical, with long sharp point; edges shallowly serrate. Unusually long and narrow.

*Color.*—Approximately Cedar Green (Plate VI) on upper surface; lighter green on under surface.

*Appearance.*—Surface smooth.

*Petiole.*—Relatively short, approximately ½ inch.

*Glands.*—Brown; large; several appear at base of leaf on upper side.

Blossoms: Large; perfect; about the same color as blossoms of Elberta and appearing at about the same time.

*The fruit*

Maturity: Late, averaging one week later than Elberta and three weeks later than South Haven.

Ripening habit: Ripens evenly.

Size: Very large; from 3 to 3½ inches in length by 3 inches in diameter.

Form: Blocky; uniform; symmetrical.

*Suture.*—Inconspicuous line, deeper at base than elsewhere.

*Cavity.*—Deep and narrow.

*Apex.*—Small; depressed; short.

Skin:

*Thickness.*—Medium.

*Texture.*—Medium in toughness but strong. No tendency to crack.

*Adherence.*—Separates easily from flesh when ripe.

*Pubescence.*—Practically fuzzless.

*Color.*—Basic color is approximately Orange Buff (Plate III), much of this surface color being overlaid with shadings of red ranging from Light Jasper Red (Plate XIII) to Vandyke Red (Plate XIII), sometimes even to Oxblood Red (Plate I). Sometimes the coloring appears merely as stripings of the red shades, but usually there is a deep red "cheek" much darker than the coloring elsewhere on the peach.

Flesh:

*Color.*—Light Orange Yellow (Plate III) to Deep Chrome (Plate III), with bright red coloring extending from the pit into the flesh. When very ripe, the flesh is Cadmium Yellow (Plate III) just beneath the skin.

*Texture.*—Fine grained; firm but melting; very juicy.

*Fibers.*—Few; do not cling to stone.

*Aroma.*—Delicate.

*Flavor.*—Different from any other peach on the market. Sweet, with slight acid undertone with something of the suggestion of pineapple or mango flavor.

*Eating quality.*—Excellent.

Stone: Free.

*Size.*—Large, 1¾ inches long, 1¼ inches wide and ⅞ inch thick.

*Surface.*—Moderately smooth, but with some deep grooves, particularly along upper edge.

*Form.*—Plump; sides equal; sharp-pointed at apex; dorsal edge deeply grooved; ventral edge winged.

*Color.*—Brown with reddish tinge on upper portion, especially on edges.

*Comparison*

This new peach variety is similar to the South Haven in several respects but the tree is more hardy and its fruit ripens later, is more free of stone, more highly colored, a better shipper, more regular in individual shape, and has a different and sweeter flavor which many think superior.

*Comparison with J. H. Hale*

A few of the more important points of difference between the new peach variety and J. H. Hale are:

1. The tree of the new variety is more hardy.
2. The tree of the new variety is more consistent in producing a heavy crop of very large fruits.
3. The maturity season for the new variety is about a week later than that of J. H. Hale.
4. The fruits are more highly colored on the new variety.
5. The fruits of the new variety have a very different flavor from the J. H. Hale (as described).
6. The fruits of the new variety have skin which is less pubescent and have a greater tendency to separate from the flesh when ripe.

Having thus disclosed my invention, I claim:

A new and useful variety of peach tree, as described, characterized particularly by its hardiness and vigor; its late maturity; and its prolific production of uniformly large freestone fruit with firm but juicy flesh, unusual flavor, and tough skin which is highly colored and practically fuzzless, as shown and described.

GEORGE R. FOWLER.